United States Patent [19]

Rhodes et al.

[11] 4,085,222
[45] Apr. 18, 1978

[54] PHARMACEUTICAL COMPOSITIONS CONTAINING 1,3-DIOXANES

[75] Inventors: Deryck Rhodes; Roger Frank Newton, both of London, England

[73] Assignee: Allen & Hanburys Limited, London, England

[21] Appl. No.: 523,238

[22] Filed: Nov. 12, 1974

[30] Foreign Application Priority Data

Nov. 21, 1973 United Kingdom ............... 53924/73

[51] Int. Cl.² ............................................. A61K 31/335
[52] U.S. Cl. ................................ 424/278; 260/329 R; 260/594; 260/340.7; 424/275
[58] Field of Search ...................... 260/340.7; 424/278

[56] References Cited

U.S. PATENT DOCUMENTS

| 3,000,905 | 9/1961 | Wheeler et al. ............... 260/340.7 |
| 3,454,596 | 7/1969 | Hamilton ..................... 260/340.7 |
| 3,506,686 | 4/1970 | Ryrfors ....................... 260/340.7 |
| 3,826,822 | 7/1974 | Moulin et al. ................. 424/278 X |

FOREIGN PATENT DOCUMENTS

| 475,546 | 7/1951 | Canada ........................ 260/340.7 |
| 2,258,013 | 11/1972 | Germany ...................... 260/340.7 |
| 4,320,012 | 8/1968 | Japan ......................... 424/278 |
| 7,104,033 | 9/1971 | Netherlands .................. 260/340.7 |
| 1,239,532 | 7/1971 | United Kingdom .............. 260/340.7 |

OTHER PUBLICATIONS

C.A. 66:104268x.
C.A. 70:10106y.
C.A. 66:85739h.
Blicke et al, J. Amer. Chem. Soc., 76 pp. 3153-3156 (1954).
Maj. Archiv. Immun. et Therap. Exper. 10, p. 925 (1962).
Pallos Studien Uber Analgetika aus der Reihe von Kernfluorierten Aromaten und Pentaerythrit, 1963, Prom. Nr. 3370, (pp. 36, 44 and 45 pertinent).
Chem. Abstracts 56:2442b.
Chem. Abstracts 56:1447a.
Chem. Abstracts 54:26015c.

Primary Examiner—Ethel G. Love
Attorney, Agent, or Firm—Bacon & Thomas

[57] ABSTRACT

Compounds of the general formula I:

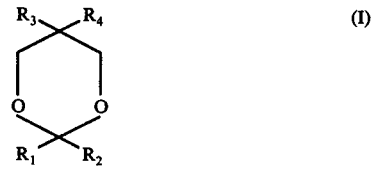

in which $R_1$ represents cycloalkyl, aralkyl, heterocyclic aryl, or substituted phenyl, in which the substituents on the phenyl group are one or more of the following groups, that is halogen, hydroxy, alkoxy ($C_1$–$C_4$), alkyl ($C_1$–$C_4$), nitro, dialkylamino or methylenedioxy;

$R_2$ represents a hydrogen atom, or together with the group $R_1$ and the adjacent carbon atom represents a cycloalkyl group with 3 to 7 carbon atoms inclusive;

$R_3$ represents a group $R_5CO$—, or $R_5CH(OH)$— in which $R_5$ is methyl or ethyl;

$R_4$ is an alkyl group ($C_1$–$C_6$) or a phenyl group; and in which where $R_4$ is alkyl, $R_3$ and $R_4$ may be linked together to produce a 5-, 6- or 7-membered spirocyclic system with the adjacent carbon atom of the dioxan ring; and where the compounds contain hydroxyl groups, esters of such compounds; and where the compounds contain basic centers, non-toxic phrmaceutically acceptable salts with organic or inorganic acids. Pharmaceutical compositions comprising the specified compounds and other related compounds. Processes for the production of the compounds. The compounds have utility as analgetics.

26 Claims, No Drawings

PHARMACEUTICAL COMPOSITIONS CONTAINING 1,3-DIOXANES

This invention relates to novel 1,3-dioxans, to a process for their production, and to compositions containing these novel 1,3-dioxans and related compounds.

We have found according to the invention that compounds of formula (I) and (Ia) below have analgetic activity. In the mouse they inhibit the writhing induced by intraperitoneal injections of phenylquinone (L. C. Hendershot and J. Forsaith, J. Pharmacol., 1959, 125, 237), and in the dog and the monkey they reduce the response to pain caused by electrical stimulation of the pulp of the tooth (C. L. Mitchell, J. Pharmacol., 1964, 146, 1). In the above tests the compounds of the invention have potencies comparable with that of paracetamol. They do not induce a Straub-tail response in the mouse and therefore differ from narcotic agents. They have no significant actions on the cardiovascular or respiratory systems of the anaesthetized dog, and are virtually non-toxic at very high doses. They differ from paracetamol in their lack of anti-pyretic properties. The compounds should be useful in man for the relief of mild pain, e.g. bursitis, toothache, headache, muscle pains etc.

According to one aspect of the invention therefore there are provided compounds of the general formula:

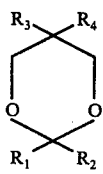

(I)

in which $R_1$ represents cycloalkyl, aralkyl, heterocyclic aryl, or substituted phenyl, in which the substituents on the phenyl group are one or more of the following groups, that is halogen, hydroxy, alkoxy ($C_1$-$C_4$), alkyl ($C_1$-$C_4$), nitro, dialkylamino or methylenedioxy;

$R_2$ represents a hydrogen atom, or together with the group $R_1$ and the adjacent carbon atom represents a cycloalkyl group with 3 to 7 carbon atoms inclusive;

$R_3$ represents a group $R_5CO$—, or $R_5CH(OH)$— in which $R_5$ is methyl or ethyl;

$R_4$ is an alkyl group ($C_1$-$C_6$) or a phenyl group; and in which where $R_4$ is alkyl, $R_3$ and $R_4$ may be linked together to produce a 5-, or 6- or 7-membered spirocyclic system with the adjacent carbon atom of the dioxan ring; and where the compounds contain hydroxyl groups, esters of such compounds; and where the compounds contain basic centres, non-toxic pharmaceutically acceptable salts with organic or inorganic acids.

As indicated the invention includes esters of compounds of formula I and esters of alkanoic acids, are particularly preferred. As an example esters on the group $R_5CH(OH)$— e.g. an acetyl ester $R_5CH(OCOCH_3)$— may be mentioned.

The invention also includes all possible stereoisomers of the compounds of the invention.

A preferred group of compounds are those of general formula (I) in which $R_1$ is a cycloalkyl group, particularly cyclohexyl, a phenyl group substituted by one or more halogen atoms, or by alkyl ($C_1$-$C_4$), alkoxy, hydroxy, nitro or dialkylamino groups; or $R_1$ is a heterocyclic group, in particular thienyl or furyl.

$R_3$ is an α-hydroxyethyl group or an acetyl group.

$R_4$ is an alkyl group ($C_1$-$C_4$) in particular a methyl group or $R_4$ and $R_5$ are linked together to produce a six-membered spirocyclic system with the dioxan ring.

Where $R_1$ is substituted phenyl the substituent on the phenyl ring is preferably in the para position.

One particularly preferred group are compounds of the general formula (II):

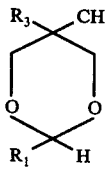

$R_1$ = phenyl substituted by Alk, OH, OAlk or —NMe$_2$ $R_3$ = COCH$_3$ or CHOHCH$_3$ (II)

Particularly preferred compounds of this class are those where $R_1$ = p-MeO.C$_6$H$_4$-, p-Me$_2$N.C$_6$H$_4$, p-MeC$_6$H$_4$ or p-HOC$_6$H$_4$.

Particularly preferred compounds are the following:

[2-(p-methylphenyl)-5-methyl-1,3-dioxan-5-yl]methyl ketone

[2-(p-hydroxyphenyl)-5-methyl-1,3-dioxan-5-yl]methyl ketone

[2-(p-methoxyphenyl)-5-methyl-1,3-dioxan-5-yl]methyl ketone

[2-(p-dimethylaminophenyl)-5-methyl-1,3-dioxan-5-yl]methyl ketone 2-(p-hydroxyphenyl)α,5-dimethyl-1,3-dioxan-5-methanol 2-(p-methoxyphenyl)α,5-dimethyl-1,3-dioxan-5-methanol 2-(p-methylphenyl)α,5-dimethyl-1,3-dioxan-5-methanol.

In another aspect of the invention there is provided a pharmaceutical composition comprising as active ingredient one or more compounds of the general formula:

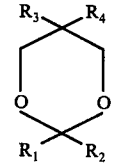

I(a)

in which $R_1$ represents a straight or branched ($C_1$-$C_6$) alkyl group, a cycloalkyl group, an aralkyl ($C_1$-$C_4$) group, a heterocyclic aryl group or an aryl group which aryl group may optionally be substituted by one or more of the following groups, that is, halogen, hydroxy, alkoxy ($C_1$-$C_4$), alkyl ($C_1$-$C_4$), nitro, dialkylamino or methylenedioxy;

$R_2$ represents a hydrogen atom, or together with the group $R_1$ and the adjacent carbon atom represents a cycloalkyl group with 3 to 7 carbon atoms inclusive;

$R_3$ represents a group $HOCH_2$—, $R_5CO$— or $R_5CH(OH)$—, where $R_5$ is methyl or ethyl;

$R_4$ is an alkyl group ($C_1$-$C_6$) or a phenyl group; and in which where $R_4$ is alkyl, $R_3$ and $R_4$ may be linked together to produce a 5-, 6- or 7-membered spirocyclic system with the adjacent carbon atom of the dioxan ring; and where the compounds contain hydroxyl groups, esters of such compounds; and where the compounds contain basic centres, non-toxic pharmaceutically acceptable salts with organic or inorganic acids; in association with a pharmaceutical carrier or diluent.

The definition of the compounds in formula I(a) is wider than in I, since we have found that there are some compounds which are not novel but which nevertheless have the pharmacological activity indicated which has not previously been described for these compounds. The invention therefore also extends to pharmaceutical compositions containing them.

A preferred class of compounds of formula I(a) which are known compounds are those in which $R_1$ is an alkyl group as defined in particular methyl or tertiary butyl or an unsubstituted aryl group in particular phenyl and $R_3$ represents $R_5CO$, or $R_5CH(OH)$— in which $R_5$ has the definition given herein.

In the case where the compound is known, the term pharmaceutical carrier or diluent will not in general extend to simple solutions in common solvents except when these solvents have been treated in a way determined by their intended pharmaceutical use.

The pharmaceutical compositions may take any convenient form and may be formulated as liquids, e.g. solutions, dispersions, or emulsions, or as solids, as desired. Compositions for oral administration as tablets, capsules and suspensions are examples of preferred formulations. Other formulations include injectable solutions and suppositories. The compounds may be administered in unit dosage form, in particular as tablets. A suitable per diem dose is in the range of 500 to 4000 mgs. The dosage units may be so formulated as to provide the whole or part of the per diem dosage in a single unit.

Other pharmacologically active ingredients, e.g. analgetics, anti-pyretics, anti-inflammatories, etc., may also form part of these compositions.

The compounds of the general formula I and I(a) may be prepared by the condensation of a 1,3-diol of the general formula (III) in which $R_4$ and $R_5$ have the above stated meaning, or are groups convertible thereto, with the appropriate aldehyde ($R_1CHO$) or cyclo-alkyl ketone ($R_1R_2CO$) in which $R_1$ and $R_2$ have the above stated meanings.

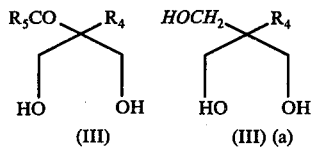

Where $R_3$ has the meaning $HO.CH_2$-, the corresponding triols (III) (a) are used as starting material. The condensation reaction may be carried out in a solvent, e.g. a hydrocarbon solvent such as benzene or toluene, in the presence of an acid catalyst such as toluene-p-sulphonic acid, and with heating if necessary. This process leads to compounds in which $R_3$ is $R_5CO$— or $HOCH_2$—.

When prepared by the route outlined above, the compounds of the invention may be obtained as a single configurational isomer or as a mixture of configurational stereoisomers. As $R_2$ represents a hydrogen atom the products are shown as (IV) and (V).

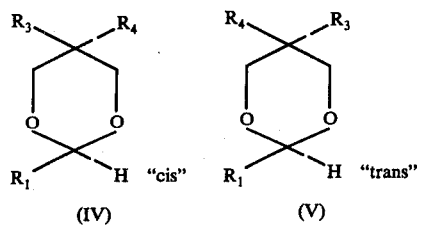

The proportion of each of the stereoisomers (IV) and (V) may be determined from the nuclear magnetic resonance spectrum. The stereoisomer (IV) in which the groups $R_1$ and $R_3$ are positioned above the same surface of the dioxan ring, is referred to as the "cis" isomer. The product of formula (V) is referred to as the "trans" isomer.

If desired, mixtures of the cis and trans isomers may be separated by standard procedures, for example by crystallisation or by gas liquid chromatography.

Compounds in which $R_3$ represents $R_5CH(OH)$— may be prepared from compounds in which $R_3$ represents $R_5CO$ by reduction. This reduction may be conveniently carried out using a complex metal hydride such as lithium aluminium hydride or sodium borohydride in a suitable solvent and with heating if necessary. In a reverse process compounds in which $R_3$ is $R_5CO$ may be prepared by oxidation of compounds in which $R_3$ is $R_5CH(OH)$— for example, chromium trioxide as the oxidising agent.

In another example, primary alcohols ($R_5 = HOCH_2$—) may be oxidised with dicyclohexylcarbodiimide in aqueous dimethyl sulphoxide to aldehydes ($R_3 = H.CO$—), which may then be converted into compounds of the invention where $R_3 = R_5CH(OH)$— by reaction with a Grignard reagent $R_5MgX$ or an alkyl lithium $R_5Li$. In turn, these compounds may be oxidised to the compounds of the invention where $R_5 = R_5CO$— as described above.

Compounds of the invention may also be converted to other compounds of the invention by reactions which change the nature of any one or more of the groups $R_1-R_4$ within the meanings given. Examples of these conversions are those given above for the group $R_3$. The invention provides therefore also a process for the production of compounds of formula I as outlined above.

The diols of formula (III) are either known compounds or may be prepared from the ketone (VI) and formaldehyde.

$$R_5CO.CH_2R_4 \qquad (VI)$$

The reaction is carried out in a solvent, in the presence of a catalyst, and with heating if necessary. Preferred solvents include water, aqueous ethanol, and aqueous dimethyl sulphoxide, and preferred catalysts include potassium carbonate, lithium hydroxide, and calcium hydroxide.

The following Examples illustrate the invention. These Examples exemplify also the production of compounds of Formula I(a) which do not fall within Formula I.

EXAMPLE 1

5-Methyl-2-(p-tolyl)1,3-dioxan-5-methanol 1,1,1-tris(Hydroxymethyl)ethane (12.0 g), p-tolualdehyde (12.0 g), benzene (100 ml) and toluene-p-sulphonic acid (100 mg) were heated under reflux in a Dean and Stark water trap until no more water separated. The benzene was removed and the crude product was crystallised from light petroleum (b.p. 60°–80°) ethyl acetate as white needles, m.p. 104.5°–105.5°. (cis:trans isomer ratio 82:18). The following compounds were prepared in a similar manner from 1,1,1-tris(hydroxymethyl)ethane and the corresponding aldehyde $R_1CHO$.

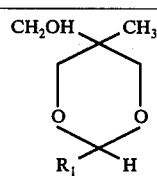

| $R_1$ | Ratio of cis:trans isomers | Physical Constants |
|---|---|---|
| —C(CH)₃S⌐⌐ | 90:10 | m.p. 91–92° (light petroleum (b.p. 60–80°)/EtOAc) |
| p-OHC₆H₄ | 100:0 | m.p. 149–152° (light petroleum (b.p. 60–80°)/EtOAc) |
| p-CH₃OC₆H₄ | 85:15 | m.p. 97–100° (light petroleum (b.p. 60–80°) toluene) |
| p-FC₆H₄ | 84:16 | m.p. 123–125° (light petroleum (b.p. 60–80°)/EtOAc) |
| p-NO₂C₆H₄ | 90:10 | m.p. 100–101° (light petroleum (b.p. 60–80°)/EtOAc |
| p-(CH₃)₂NC₆H₄ | 70:30 | m.p. 106° (light petroleum (b.p. 60–80°)/EtOAc) |
| p-ClC₆H₄ | 86:14 | m.p. 103–104° (light petroleum (b.p. 60–80°)/EtOAc) |
| 3,4-Cl₂C₆H₃ | 50:50 | m.p. 91–94° (light petroleum (b.p. 60–80°)/EtOAc) |
| m-ClC₆H₄ | 78:22 | m.p. 73° (light petroleum (b.p. 60–80° C)/EtOAc) |
| m-CH₃C₆H₄ | 76:24 | m.p. 52° (light petroleum (b.p. 60–80°)/EtOAc) |

EXAMPLE 2

[2-(p-Fluorophenyl)-5-methyl-1,3-dioxan-5-yl]methyl ketone 3,3-bis(Hydroxymethyl)butanone (13.2 g), p-fluorobenzaldehyde (12.4 g), benzene (100 ml) and toluene-p-sulphonic acid (100 mg) were heated under reflux in a Dean and Stark water trap until no more water separated. The benzene was removed and the crude oily residue was triturated with light petroleum (b.p.40°–60°) to give an off-white crystalline solid.

Crystallisation from light petroleum (b.p.60°–80°) afforded white needles m.p.81°.

The following compounds were prepared in a similar manner from 3,3-bis(hydroxymethyl)butanone and the aldehyde $R_1CHO$.

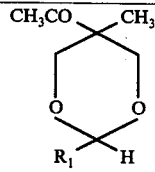

| $R_1$ | Ratio of cis:trans isomers | Physical Constants |
|---|---|---|
| p-CH₃C₆H₄ | 100:0 | m.p. 100° (light petroleum (b.p.60–80°) EtOAc) |
| p-ClC₆H₄ | 100:0 | m.p.126.5° (diethyl ether) |
| 3,4-Cl₂C₆H₃ | 100:0 | m.p.70° (light petroleum (b.p.40–60°) EtOAc) |
| m-ClC₆H₄ | 64:36 | m.p.65° (light petroleum (b.p.60–80°) EtOAc) |
| m-BrC₆H₄ | 100:0 | m.p.89° (light petroleum (b.p.60–80°)/EtOAc) |
| m-CH₃C₆H₄ | 64:36 | b.p.138–141°/0.05 torr |
| m-NO₂C₆H₄ | 100:0 | m.p.79° (diethyl ether) |
| o-CH₃C₆H₄ | 100:0 | m.p.102° (diethyl ether) |
| o-ClC₆H₄ | 100:0 | m.p.99° (light petroleum (b.p.60–80°)/EtOAc) |
| C₂H₅ | 72:25 | b.p.73–75°/0.2 torr |
| CH(CH₃)₂ | 70:30 | b.p.80–81°/0.05 torr |
| cyclo C₆H₁₁ | 74:26 | b.p.106–110°/0.6 torr |
| —C(CH)₃S⌐⌐ | 94:6 | m.p.60–63° (light petroleum (b.p.60–80°) EtOAc) |
| CH₂C₆H₅ | 68:32 | b.p.134–136°/0.07 torr |
| p-OHC₆H₄ | 100:0 | m.p.137° (diethyl ether) |
| p-NO₂C₆H₄ | 100:0 | m.p.102° (cyclohexane/EtOAc) |
| p-Et₂NC₆H₄ | 100:0 | m.p.73–4° (diethylether/light petroleum (b.p. 60–80°) |
| p-EtOC₆H₄ | 82:18 | m.p.46–54° (diethyl ether |
| 3,4—OCH₂OC₆H₃ | 100:0 | m.p.110–1° (light petroleum (b.p.60–80°)) |
| C(CH)₃O⌐⌐ | 94:6 | m.p.79–82° (light petroleum (b.p.60–80°)/EtOAc) |
| 3,4—OMeC₆H₃ | 79:21 | b.p.180°/0.01 torr m.p.56.5–77° (light petroleum (b.p.60–80°0/EtOAc) |
| 3,4—OH,OMeC₆H₃ | 100:0 | m.p. 118–119.5° (light petroleum (b.p.60–80°)/EtOAc) |

EXAMPLE 3

[2-(p-Methoxyphenyl)-5-methyl-1,3-dioxan-5-yl]methyl ketone 3,3-bis(Hydroxymethyl)butanone (39.6 g), benzene (200 ml), anisaldehyde (40.8) and toluene-p-sulphonic acid (200 mg) were heated under reflux in a Dean and Stark water trap until the theoretical amount of water had separated. The solution was concentrated in vacuo and the solid residue was crystallised from isopropyl acetate as a white crystalline solid m.p. 112°–114°, cis isomer.

EXAMPLE 4

[2-(p-Dimethylaminophenyl)-5-methyl-1,3-dioxan-5-yl]methyl ketone 3,3-bis(Hydroxymethyl)butanone (29.0 g), p-dimethylaminobenzaldehyde (29.8 g), toluene-p-sulphonic acid (250 mg) and toluene (140 ml) were heated under reflux in a Dean and Stark water trap until the theoretical amount of water had separated. The solution was concentrated in vacuo, the crude residue was washed with 8% aqueous sodium bicarbonate solution (100 ml) and crystallised from petroleum ether (b.p. 80°-100°-)/ethyl acetate as a crystalline solid m.p.118°-120° (Cis-trans 96:4).

EXAMPLE 5

[2,2'-Spirocyclopentyl-5-methyl-1,3-dioxan-5-yl]methyl ketone 3,3-bis(Hydroxymethyl)butanone (19.8 g), cyclopentanone (12.6 g) toluene-p-sulphonic acid (100 mg) and benzene (100 ml) were heated under reflux in a Dean and Stark water trap until the theoretical amount of water had been collected. The benzene solution was shaken (Na₂SO₄) and concentrated at reduced pressure. The residue was distilled to give a colourless mobile oil b.p.91°-93°/0.05 torr.

[2,2'-Spirocyclohexyl-5-methyl-1,3-dioxan-5-yl]methyl ketone b.p.94°-96°/0.01 torr was prepared in a similar manner starting from cyclohexanone.

EXAMPLE 6

[5-Pentyl-2-methyl-1,3-dioxan-5-yl]methyl ketone (a) 3,3-bis(Hydroxymethyl)-2-octanone 2N Lithium hydroxide solution (1.0 ml) was added to a stirred solution of 2-octanone (4.5 g) and 36% aqueous formaldehyde (6.0 ml) in methanol (10 ml). The temperature was maintained at 10°-15° during the addition and then gradually allowed to rise to room temperature. After stirring for 48 hr, ether (50 ml) and brine (20 ml) were added and the layers separated. The aqueous layer was extracted with ethyl acetate (3 × 25 ml) and the combined extracts were dried (Na₂SO₄) and concentrated. The residue distilled to give a colourless oil b.p.100°-110°/0.05 torr.

(b) [5-Pentyl-2-methyl-1,3-dioxan-5-yl]methyl ketone

A solution of 3,3-bis(hydroxymethyl)-2-octanone (9.4 g), acetaldehyde (4.4 g) and toluene-p-sulphonic acid (35 mg) in benzene (175 ml) was allowed to stand for 4 hrs. The solution was then heated under reflux in a Dean and Stark water trap until no more water separated. The cooled solution was washed with 10% sodium carbonate solution, dried (Na₂SO₄) and concentrated. The residue was distilled to give a colourless oil b.p.93°-100°/0.7 torr (cis:trans isomer ratio 75:25).

The following compounds were prepared in a similar manner from the corresponding ketones R₅COCH₂R₄, formaldehyde and the corresponding aldehyde R₁CHO.

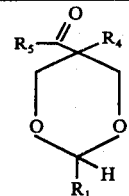

| R₁ | R₄ | R₅ | Ratio of cis:trans isomers | Physical Constants |
|---|---|---|---|---|
| Ph | Me | Et | 100:0 | m.p.57-9° (light petroleum (b.p.40-60°)) |
| Ph | Et | Me | 70:30 | b.p.123-130°/0.05 torr |
| Ph | Ph | Me | 100:0 | m.p.123-4° (light petroleum (b.p.60-80°)/ethyl acetate |
| Me | Ph | Me | 73:27 | b.p.110-15°/0.05 torr |

-continued

| R₁ | R₄ | R₅ | Ratio of cis:trans isomers | Physical Constants |
|---|---|---|---|---|
| C₆H₅ | Ph | Me | 100:0 | m.p.123-124° (light petroleum (b.p.60-80°)/EtOAc) |
| 3,4-OCH₂OC₆H₃ | Ph | Me | 100:0 | m.p.117-122.5° (light petroleum (b.p.60-80°)/EtOAc) |
| p-(CH₃)₂NC₆H₄ | Ph | Me | 100:0 | m.p.148-151° (light petroleum (b.p.60-80°)/EtOAc) |
| p-ClC₆H₄ | Ph | Me | 100:0 | m.p.160-166° (light petroleum (b.p. 60-80°)/EtOAc) |
| p-MeOC₆H₄ | Ph | Me | 100:0 | m.p.125.5-126.5° (light petroleum (b.p.60-80°)/EtOAc) |
| p-NO₂C₆H₄ | Ph | Me | 100:0 | m.p.146-149° (light petroleum (b.p.60-80°)/EtOAc) |
| p-OHC₆H₄ | Ph | Me | 100:0 | m.p.172-178.5° (light petroleum (b.p.60-80°)/EtOAc) |
| CH(CH)₃O | Ph | Me | 85:15 | m.p.98-100° (light petroleum (b.p.60-80°)/EtOAc) |
| CH(CH)₃S | Ph | Me | 71:29 | m.p.129-134° (light petroleum (b.p.60-80°)/EtOAc), |
| CH₂PH | Ph | Me | 72:28 | b.p.180-190°/0.6 torr |

EXAMPLE 7

2(p-Fluorophenyl)α,5-dimethyl-1,3-dioxan-5-methanol 2-(p-Fluorophenyl)-5-methyl-1,3-dioxan-5-yl-methyl ketone (11.85 g) in dry ether (100 ml) was added to a slurry of lithium aluminium hydride (2.5 g) in dry ether (50 ml) and the mixture was heated under reflux for 4 hours. Moist tetrahydrofuran (20 ml) was added and the mixture was filtered. The filtrate was concentrated and the crude product was recrystallised from ethyl acetate/light petroleum (b.p. 60°-80°) as white crystals, m.p.78°, of the pure cis isomer.

The following compounds were prepared in a similar manner by the reduction of the corresponding ketone.

| R₁ | R₄ | Ratio of cis:trans isomers | Physical Constants |
|---|---|---|---|
| 3,4-Cl₂C₆H₃ | CH₃ | 100:0 | m.p.84° (light petroleum (b.p.60-80°)/EtOAc) |
| m-ClC₆H₄ | CH₃ | 100:0 | m.p.72° (light petroleum (b.p.60-80°)/EtOAc) |
| m-CH₃C₆H₄ | CH₃ | 100:0 | m.p. 79° (light petroleum (b.p.60-80°) |
| o-CH₃C₆H₄ | CH₃ | 100:0 | m.p.119.5° (light petroleum (b.p.60-80°)/EtOAc) |
| o-ClC₆H₄ | CH₃ | 100:0 | m.p.117° (light petroleum (b.p.60-80°)/ |

-continued $$\text{CH}_3\text{CHOH} \diagdown \text{R}_4$$ on 1,3-dioxane ring with R_1 and H

| R₁ | R₄ | Ratio of cis:trans isomers | Physical Constants |
|---|---|---|---|
| m-BrC₆H₄ | CH₃ | 100:0 | m.p.74° (light petroleum (b.p.60–80°)/EtOAc) |
| CH₃ | CH₃ | 82:18 | b.p.73–76°/0.2 torr |
| C₂H₅ | CH₃ | 76:24 | b.p.69–71°/0.3 torr |
| CH(CH₃)₂ | CH₃ | 70:30 | b.p.86–88°/1.5 torr |
| cyclo C₆H₁₁ | CH₃ | 74:26 | b.p.110–116°/0.3 torr |
| CH₂C₆H₅ | CH₃ | 68:32 | b.p.122–125°/0.1 torr |
| C(CH₃)S (cyclic) | CH₃ | 100:0 | m.p.87–88° (light petroleum (b.p.60–80°)/EtOAc) |
| p-OHC₆H₄ | CH₃ | 100:0 | m.p.164° (light petroleum (b.p.40–60°)/EtOAc) |
| p-CH₃OC₆H₄ | CH₃ | 100:0 | m.p.87° (light petroleum (b.p.60–80°)/diethyl ether) |
| p-CH₃C₆H₄ | CH₃ | 100:0 | m.p.116° (light petroleum (b.p.60–80°) |
| p-ClC₆H₄ | CH₃ | 100:0 | m.p.120° (light petroleum (b.p.60–80°)/diethyl ether) |
| p-FC₆H₄ | CH₃ | 100:0 | m.p.78° (light petroleum (b.p.60–80°) |
| C(CH)₃O (cyclic) | CH₃ | 100:0 | m.p.71.5–73° (light petroleum (b.p.60–80°) |
| 3,4-OMeC₆H₃ | CH₃ | 75:25 | b.p.180–120°/0.05 torr with decomposition. |
| 3,4-OH,OMeC₆H₃ | CH₃ | 100:0 | m.p.134–136° (light petroleum (b.p.60–80°)/EtOAc) |
| C₆H₅ | Ph | 100:0 | m.p.138–139° (light petroleum (b.p.60–80°)/EtOAc) |
| 3,4-OCH₂OC₆H₃ | Ph | 100:0 | m.p.125–127° (light petroleum (b.p.60–80°)/EtOAc) |
| p-(CH₃)₂NC₆H₄ | Ph | 100:0 | m.p.140.5–145.5 (light petroleum (b.p.60–80°)/benzene) |
| p-ClC₆H₄ | Ph | 100:0 | m.p.128.5–130° (light petroleum (b.p.60–80°)/EtOAc) |
| p-MeOC₆H₄ | Ph | 100:0 | m.p.131–132° (light petroleum (b.p.60–80°)/EtOAc) |
| p-NO₂C₆H₄ | Ph | 100:0 | m.p.145.5–148.5° (light petroleum (b.p.60–80°)/EtOAc) |
| p-OHC₆H₄ | Ph | 100:0 | m.p.118–221° (methanol) |
| C(CH)₃O (cyclic) | Ph | 100:0 | m.p.105–106° (light petroleum (b.p.60–80°)/EtOAc) |
| C(CH)₃S (cyclic) | Ph | 100:0 | m.p.125–128.5° (light petroleum (b.p.60–80°)/EtOAc) |
| CH₂C₆H₅ | Ph | 100:0 | m.p.91.5–92.5° (light petroleum (b.p.60–80°) |

EXAMPLE 8

α,5-Dimethyl-2-(m-nitrophenyl)1,3-dioxan-5-methanol

To a solution of 5-methyl-2-(m-nitrophenyl)1,3-dioxan-5-yl methyl ketone (9.0 g) in methanol (100 ml) was added a solution of sodium borohydride (4.5 g) in water (20 ml). The mixture was heated under reflux for 1 hour, methanol was removed in vacuo and the residue was extracted with ether (3 × 100 ml). The extracts were dried (Na₂SO₄) and concentrated and the residue was crystallised from diethyl ether as pale yellow crystals m.p. 97°, cis isomer.

EXAMPLE 9

α,5-Dimethyl-2,2'-spiro(cyclohexyl)1,3-dioxan-5-methanol

A solution of [2,2'-spirocyclohexyl-5-methyl-1,3-dioxan-5-yl]methyl ketone (5.15 g) in dry ether (50 ml) was added to a slurry of lithium aluminium hydride (2.0 g) in dry ether (50 ml) and the mixture was heated under reflux for 4 hours. Moist tetrahydrofuran (20 ml) was added and the mixture filtered. The filtrate was dried (Na₂SO₄) and concentrated and the residue distilled as a colourless viscous oil b.p. 106°–110°/0.3 torr.

EXAMPLE 10

2'-Phenylspiro[cycloheptane-1,5'-m-dioxan]-2-one 2,2-bis(Hydroxymethyl)cycloheptanone (1.72 g), benzaldehyde (1.06 g), benzene (75 ml) and toluene-p-sulphonic acid (100 mg) were heated under reflux in a Dean and Stark water trap until no more water separated. The benzene was removed and the residue was crystallised from light petroleum (b.p. 60°–80°) as colourless pyramids m.p. 95°–97° (cis:trans 2:98).

2'-Methyl-spiro[cycloheptane-1,5'-m-dioxan]-2-one b.p. 119°–120° (cis:trans 23:77) was prepared in a similar manner.

The following compounds were prepared in a similar manner from the bis(hydroxymethyl)ketones and the aldehydes R₁-CHO.

spiro dioxane structure with (CH₂)ₙ and R₁

| R₁ | n | Ratio of cis:trans isomers | Physical Constants |
|---|---|---|---|
| Me | 5 | 27:73 | b.p.116–9°/1.5 torr |
| Ph | 3 | 0:100 | m.p.92.5–94.5° (light petroleum (b.p.60–80°) |
| iPr | 5 | 10:90 | m.p.58–60° (light petroleum (b.p.60–80°) |
| Me | 3 | 0:100 | b.p.60–64°/0.4 torr |
| —CH₂Ph | 5 | 44:56 | b.p.152–6°/0.05 torr |
| HOC₆H₄ | 5 | 0:100 | m.p.138.5°–140° (ethyl acetate/light petroleum (b.p.60–80°) |
| HOC₆H₄ | 5 | 100:0 | m.p.161–163° (ethyl acetate/light (petroleum (b.p.60–80°) |

EXAMPLE 11

Dispiro[cyclohexane-1,2'-m-dioxan-5',1''-cycloheptane]-2'-one 2,2-bis(Hydroxymethyl)cycloheptanone (3.44 g), cyclohexanone (1.96 g), toluene-p-sulphonic acid (50 mg) were heated under reflux in dry benzene (75 ml) in a Dean and Stark water trap until no more water separated. The cooled benzene solution was washed with 8% sodium bicarbonate solution, dried (Na₂SO₄) and concentrated. The residual yellow oil which solidified on standing was recrystallised from light petroleum (b.p. <40°) to afford colourless crystals m.p.52°–54°.

EXAMPLE 12

2'-Phenyl-spiro[cycloheptane-1,5'-m-dioxan]-2-ol

2'-Phenyl-spiro[cycloheptane-1,5'-m-dioxan]-2-one (2.35 g) in dry tetrahydrofuran (40 ml) was added dropwise and with stirring to a slurry of lithium aluminium hydride (0.6 g) in dry tetrahydrofuran (100 ml). The mixture was refluxed for 4 hours, moist tetrahydrofuran (10 ml) was added and the mixture was filtered. The filtrate was concentrated and the crude product was crystallised from light petroleum (b.p. 60°-80°)/ethyl acetate as colourless crystals m.p.125°-127° (cis:trans 1:99).

2'-Methyl-spiro[cycloheptane-1,5'-m-dioxan]-2-ol b.p. 98°-100°/1.5 torr (cis:trans 23:77) and 2'-phenyl-spiro[cyclopentane-1,5'-m-dioxan]-2-ol m.p.62°-70° (ethyl acetatepetroleum ether (b.p. 60°-80°)) trans isomer, were prepared in a similar manner.

EXAMPLE 13

Dispiro[cyclohexane-1,2'-m-dioxane-5'-1''-cycloheptane]-2''-ol

Dispiro[cyclohexane-1,2'-m-dioxan-5', 1''-cycloheptane]-2''-one (1.2 g) in dry tetrahydrofuran (10 ml) was added to a slurry of lithium aluminium hydride (0.4 g) in dry tetrahydrofuran (50 ml). The mixture was heated under reflux for 4 hours and treated with moist tetrahydrofuran (10 ml). The mixture was filtered and the filtrate concentrated to afford the crude product which was recrystallised from light petroleum (b.p. <40°) to give colourless crystals m.p. 61°-64°.

EXAMPLE 14

2-[4-(Dimethylamino)phenyl]-α,5-dimethyl-1,3-dioxan-5-methanol acetate

2-[4-(Dimethylamino)phenyl]-α,5-dimethyl-1,3-dioxan-5-methanol (195 mg), dry pyridine (2.0 ml), and acetyl chloride (1.0 ml), in benzene (10 ml) were refluxed for 3 hrs. The cooled mixture was poured into water and extracted with ethyl acetate. The combined extracts were washed with water, dried (MgSO$_4$), and evaporated. The residue was purified by preparative layer chromatography on silica gel (eluting with benzeneethyl acetate 5:1) and distilled to give an oil, b.p. 155°-160°/0.05 torr.

EXAMPLE 15

Pharmaceutical Compositions

In these compositions the compound referred to as the active compound is [2-(p-methoxyphenyl)-5-methyl-1,3-dioxan-5-yl]methyl ketone, prepared according to Example 3.

Tablets

To prepare 10,000 each containing 500 mg of active compound

Mix together 5 kilos of powdered active compound with one kilo of lactose and 0.5 kilo of maize starch. Add a sufficient quantity of a 2% aqueous solution of sodium carboxy methyl cellulose to produce a damp, cohesive mass. Granulate the mass by passing through a No. 8 British Standard (B.S.S.) sieve and drying at 50° C in a fluid-bed dryer. Pass the dry granules through a No. 16 (B.S.S.) sieve and mix with 0.25 kilo maize starch and 30 grammes of magnesium stearate. Compress the lubricated granules in a suitable tabletting machine so that each tablet weighs about 710 mg and is 13 mm in diameter.

To prepare 10,000 each containing 250 mg of active compound

Mix together 2.5 kilos of powdered active compound 250 grammes of microcrystalline cellulose B.P.C. and 0.5 kilo of Encompress. Encompress is a proprietary brand of spray-dried calcium phosphate dihydrate, with 30 grammes of magnesium stearate. Compress the mixed powder on a suitable tabletting machine to produce tablets each weighing about 330 mg and 10 mm in diameter.

Capsules

To prepare hard gelatin capsules each containing 100 mg of active compound

Mix the required quantity of active compound with sufficient microcrystalline cellulose to enable an adequate fill to be obtained in a No. 1 size hard gelatine capsule. Capsules of up to 250 mg can be prepared.

Oral Suspension

Prepare a 1% gel of Carbopol 934, which is a proprietary brand of carboxyvinyl polymer, by dispersing the required quantity of Carbopol 934 in water and adjusting the pH to 7 with dilute sodium hydroxide solution. Carefully disperse in this gel sufficient finely powdered active compound so that each 5ml contains 250 mg active compound. The gel is flavoured with suitable flavouring and sweetening agents and will contain a mixture of alkyl parahydroxybenzoates as preservative.

The active compound may be replaced by any compound of formula I(a) for example α,5-dimethyl-2-phenyl-1,3-dioxan-5-methanol, which is a known compound, the production of which is described by Morgan and Griffith, J. Chem. Soc. 841, 1937.

We claim:

1. Compounds of the formula

in which $R_1$ represents cycloalkyl, aralkyl, or substituted phenyl, in which the substituents on the phenyl group are one or more of the following groups, halogen, hydroxy, alkoxy ($C_1$–$C_4$), alkyl ($C_1$–$C_4$), nitro, or dialkylamino; $R_2$ represents a hydrogen atom, or $R_1$ and $R_2$ together with the adjacent carbon atom represent a cycloalkyl group with 3 to 7 carbon atoms inclusive; $R_3$ represents a group $R_5$CO—, or $R_5$CH(OH)— in which $R_5$ is methyl or ethyl; $R_4$ is an alkyl group ($C_1$–$C_6$) or a phenyl group; and in which where $R_4$ is alkyl, $R_3$ and $R_4$ may be linked together to produce a 5-, 6- or 7-membered hydrocarbyl spirocyclic system with the adjacent carbon atom of the dioxan ring; and where the compounds contain hydroxyl groups, esters with alkanoic acids of such compounds; and where the compounds contain basic centres, non-toxic pharmaceutically acceptable salts with organic or inorganic salts.

2. Compounds as claimed in claim 1 in which $R_1$ represents cyclohexyl or a substituted phenyl group in which the substituent is para to the bond between the phenyl nucleus and the dioxan moiety.

3. Compounds as claimed in claim 1 in which $R_3$ is an α-hydroxyethyl group or an acetyl group.

4. Compounds as claimed in claim 1 in which $R_4$ represents a methyl group or $R_4$ and $R_5$ are linked together to produce a six-membered spirocyclic system with the dioxan ring.

5. Compounds as claimed in claim 1 of the structure:

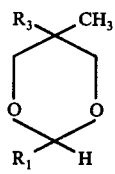

(II)

in which
$R_1$ represents a phenyl group substituted by an alkyl ($C_1$-$C_4$) group, a hydroxy group, an alkoxy ($C_1$-$C_4$) group or a dimethylamino group and
$R_3$ represents —COCH$_3$ or —CHOHCH$_3$.

6. Compounds as claimed in claim 5 in which $R_1$ represents p-CH$_3$O.C$_6$H$_4$—, p-(CH$_3$)$_2$N.C$_6$H$_4$—, p-CH$_3$C$_6$H$_4$— or p-HOC$_6$H$_4$—.

7. The compound of claim 1 which is 2-(p-hydroxyphenyl)-α,5-dimethyl-1,3-dioxan-5-methanol.

8. The compound of claim 1 which is 2-(p-methoxyphenyl)α,5-dimethyl-1,3-dioxan-5-methanol.

9. The compound of claim 1 which is 2-(p-methylphenyl)α,5-dimethyl-1,3-dioxan-5-methanol.

10. Compounds of the formula I:

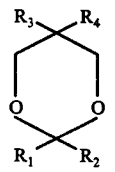

(I)

in which $R_1$ represents substituted phenyl, in which the substituents on the phenyl group are one or more of the following groups, halogen, hydroxy, alkoxy ($C_1$-$C_4$), alkyl ($C_1$-$C_4$), nitro or dialkylamino; $R_2$ represents a hydrogen atom, or $R_1$ and $R_2$ together with the adjacent carbon atom represent a cycloalkyl group with 3 to 7 carbon atoms inclusive, $R_3$ represents a group $R_5$CO— or $R_5$CH(OH)— in which $R_5$ is methyl or ethyl; $R_4$ is an alkyl group ($C_1$-$C_6$) or a phenyl group; and in which where $R_4$ is alkyl, $R_3$ and $R_4$ may be linked together to produce a 5-, 6- or 7-membered hydrocarbyl spirocyclic system with the adjacent carbon atom of the dioxan ring; and where the compounds contain hydroxyl groups, esters with alkanoic acids of such compounds; and where the compounds contain basic centres, non-toxic pharmaceutically acceptable salts with organic or inorganic salts.

11. The compound of claim 10 which is [2-(p-methylphenyl)-5-methyl-1,3-dioxan-5-yl]methyl ketone.

12. The compound of claim 10 which is [2-(p-hydroxyphenyl)-5-methyl-1,3-dioxan-5-yl]methyl ketone.

13. The compound of claim 10 which is [2-(p-methoxyphenyl)-5-methyl-1,3-dioxan-5-yl]methyl ketone.

14. The compound of claim 10 which is [2-(p-dimethylaminophenyl)-5-methyl-1,3-dioxan-5-yl]methyl ketone.

15. A pharmaceutical composition comprising as active ingredient one or more compounds of the formula:

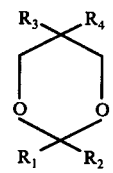

I(a)

in which $R_1$ represents a straight or branched ($C_1$-$C_6$) alkyl group, a cycloalkyl group, an aralkyl ($C_1$-$C_4$) group, or phenyl group, which phenyl group may optionally be substituted by one or more of the following groups, halogen, hydroxy, alkoxy ($C_1$-$C_4$), alkyl ($C_1$-$C_4$), nitro or dialkylamino; $R_2$ represents a hydrogen atom, or $R_1$ and $R_2$ together with the adjacent carbon atom represent a cycloalkyl group with 3 to 7 carbon atoms inclusive; $R_3$ represents a group HOCH$_2$—, $R_5$CO— or $R_5$CH(OH)—, where $R_5$ is methyl or ethyl; $R_4$ is an alkyl group ($C_1$-$C_6$) or a phenyl group; and in which where $R_4$ is alkyl, $R_3$ and $R_4$ may be linked together to produce a 5-, 6- or 7-membered hydrocarbyl spirocyclic system with the adjacent carbon atom of the dioxan ring; and where the compounds contain hydroxyl groups, esters with alkanoic acids of such compounds; and where the compounds contain basic centres, non-toxic pharmaceutically acceptable salts with organic or inorganic acids; in a pain relieving effective amount in association with a pharmaceutical carrier or diluent.

16. A composition as claimed in claim 15 in which $R_1$ is an alkyl group or an unsubstituted phenyl group and $R_3$ represents $R_5$CO— or $R_5$CH(OH)— in which $R_5$ has the meaning given in claim 15.

17. A composition as claimed in claim 16 in which $R_1$ is methyl, tertiary butyl or phenyl.

18. A composition as claimed in claim 17 in which the groups $R_1$-$R_5$ have the meanings given in claim 1.

19. A composition as claimed in claim 15 in which the group $R_1$ represents cyclohexyl or a substituted phenyl group in which the substituent is para to the bond between the phenyl nucleus and the dioxan moiety.

20. A composition as claimed in claim 15, in which the active ingredient is a compound as claimed in claim 5.

21. A composition as claimed in claim 15, in a form suitable for oral administration.

22. A composition as claimed in claim 21 in the form of a tablet, capsule or suspension.

23. A composition as claimed in claim 22 in dosage unit form each dosage unit containing the whole or part of a per diem dose of 500–4000 mgs.

24. A composition as claimed in claim 23 each dosage unit containing from 50 mg to 1 g of active ingredient.

25. A composition as claimed in claim 24 each dosage unit containing from 100 to 500 mg of active ingredient.

26. A method of relieving pain which comprises administering a pain-relieving effective amount to a patient suffering from pain a compound as defined in claim 15.

* * * * *